United States Patent [19]

Grundy et al.

[11] Patent Number: 5,405,346
[45] Date of Patent: Apr. 11, 1995

[54] TUNABLE MICROWAVE ABLATION CATHETER

[75] Inventors: David A. Grundy, Fremont; Glen G. Warner, Morgan Hill; R. Hardwin Mead, Palo Alto, all of Calif.

[73] Assignee: Fidus Medical Technology Corporation, Fremont, Calif.

[21] Appl. No.: 163,178

[22] Filed: Dec. 3, 1993

Related U.S. Application Data

[63] Continuation-in-part of Ser. No. 62,637, May 14, 1993, Pat. No. 5,364,392.

[51] Int. Cl.⁶ .............................................. A61B 17/39
[52] U.S. Cl. .................................... 606/41; 606/33; 606/34; 606/42; 607/101; 607/156
[58] Field of Search ............... 606/41, 42, 45–50, 606/33–35, 37–40; 607/100–102, 115, 116, 154–156

[56] References Cited

U.S. PATENT DOCUMENTS

| | | |
|---|---|---|
| 4,244,371 | 1/1981 | Farin . |
| 4,416,276 | 11/1983 | Newton et al. . |
| 4,494,539 | 1/1985 | Zenitani et al. . |
| 4,641,649 | 2/1987 | Walinsky et al. . |
| 4,657,015 | 4/1987 | Irnich . |
| 4,924,863 | 5/1990 | Sterzer . |
| 5,019,076 | 5/1991 | Yamanashi et al. . |
| 5,045,056 | 9/1991 | Behl . |
| 5,100,388 | 3/1992 | Behl et al. . |
| 5,150,717 | 9/1992 | Rosen et al. . |
| 5,172,699 | 12/1992 | Svenson et al. . |
| 5,188,122 | 2/1993 | Phipps et al. . |
| 5,246,438 | 9/1993 | Langberg . |
| 5,300,099 | 4/1994 | Rudie ................................ 606/41 |

FOREIGN PATENT DOCUMENTS

| | | |
|---|---|---|
| WO93/08757 | 5/1993 | WIPO . |
| WO93/20767 | 10/1993 | WIPO . |
| WO93/20768 | 10/1993 | WIPO . |
| WO93/20886 | 10/1993 | WIPO . |
| WO93/20893 | 10/1993 | WIPO . |

OTHER PUBLICATIONS

Landberg et al., "Catheter Ablation of the Artrioventricular Junction Using a Helical Microwave Antenna: A Novel Means of Coupling Energy to the Endocardium", PACE, vol. 14, Dec. 1991, pp. 2105–2113.

*Primary Examiner*—Stephen C. Pellegrino
*Assistant Examiner*—Michael Peffley
*Attorney, Agent, or Firm*—Hickman & Beyer

[57] ABSTRACT

An ablation catheter is disclosed that include a mechanism for altering the impedance of the antenna during use in a controlled manner to tune the catheter. The impedance tuning may be accomplished in a variety of manners including altering the electromechanical configuration of the antenna and moving a material relative to the antenna or vice versa in order to vary the effective impedance during use. In a preferred embodiment, the ablation catheter transmits energy in the microwave frequencies and uses a coaxial transmission line as its waveguide. The antenna is preferably helical in nature and is carried by the distal end of the transmission line.

29 Claims, 8 Drawing Sheets

TUNABLE MICROWAVE ABLATION CATHETER

This application is a Continuation-in-Part of application Ser. No. 08/062,637 filed May 14, 1993, now U.S. Pat. No. 5,364,392, which is incorporated herein by reference.

BACKGROUND OF THE INVENTION

The present invention relates generally to ablation catheter systems that use electromagnetic energy to ablate internal bodily materials. More particularly, a tunable catheter arrangement particularly suited for use in ablation systems that operate at microwave frequencies is disclosed.

Catheter ablation has recently become an important therapy for certain cardiac arrhythmias. Radio frequency (RF) energy is presently accepted as the preferred ablating energy source. Accordingly, a variety of RF catheters and power supplies are currently available to electrophysiologists. Radio frequency energy has several limitations including the rapid dissipation of energy in surface tissues resulting in shallow "burns" and failure to access deeper arrhythmogenic tissues. Another limitation is the risk of clot formation on the energy emitting electrodes. Such clots have an associated danger of causing potentially lethal strokes in the event that a clot is dislodged from the catheter. For these and other reasons, significant attention has been given recently to alternative ablative energy sources.

A second common ablation approach is the use of high voltage, direct current defibrillator discharges. Direct current ablation has several drawbacks including the need for general anesthesia and explosive discharges that can cause debris or even rupture of certain cardiac organs.

Microwave frequency energy has long been recognized as an effective energy source for heating of biological tissues and has seen use in such hyperthermia applications as cancer treatment and preheating of blood prior to infusions. Accordingly, in view of the drawbacks of the traditional catheter ablation techniques, there has recently been an interest in using microwave energy as an ablation energy source. The advantage of microwave energy is that it is much easier to control and safer than direct current applications and it is capable of generating substantially larger lesions than RF catheters, which greatly simplifies the actual ablation procedures.

In U.S. Pat. No. 4,641,649, Walinsky et al. disclose a medical procedure for the treatment of tachycardia and cardiac disrhythmia which uses microwave frequency electro magnetic energy to ablate selected cardiac tissue. The microwave energy is transmitted over a coaxial transmission line having an antenna at its distal end. A similar procedure is disclosed in Langberg et al's article entitled "Catheter Ablation of the Atrioventricular Junction Using a Helical Microwave Antenna: A Novel Means of Coupling Energy to the Endocardium," *PACE*, pp. 2105-2113 Vol. 14 (1991). As suggested in the title, the Langberg et al. proposes the use of a helical microwave antenna at the distal end of the catheter in order to improve the catheter's power delivery characteristics.

In U.S. Pat. Nos. 4,945,912, and 5,246,438, Langberg details particular helical antenna designs to be used for cardiac tissue ablation. In the disclosed design, a distal electrode is directly coupled to the antenna by a peripheral terminal. A bypass capacitor is also coupled to the peripheral terminal in an attempt to ground RF energy before it reaches the distal electrode. Although the arrangement disclosed by Langberg may have many advantages, the antenna is directly coupled to an electrode. Therefore, there is a risk that the grounding will not always be 100% effective and that this device may suffer some of the same limitations of the RF devices such as charring. In the later patent, Langberg recognizes the importance of adjusting the catheter impedance for particular ablation conditions. However, he proposes setting a particular presumed optimal impedance during fabrication. However, this design is not real-time tunable to compensate for the time variation of the impedance over the course of an ablation procedure.

Catheter diameters in cardiac ablation applications are typically restricted to diameters of about $7\frac{1}{2}$ French (approximately 2.5 mm in diameter). One problem that arises when using the very small diameter transmission lines that are necessitated by such diameter limitations is that the attenuation is quite large over the length of the transmission line. More troublesome is that during use, this attenuation can result in significant heat generation in the transmission line and catheter.

A frequent concern in the management of microwave energy is impedance matching of the various transmission line components. An impedance mismatch will reflect some portion of the incident power resulting in reduced energy transmission and increased losses, typically manifested as heat generation due to line or wave guide attenuation. The effects of these mismatches can be minimized through a process of "impedance matching" with the use of a variety of tuning device configurations and methods. Efficient use of these methods mandates close proximity of the device with the source of the reflected power.

With microwave energy ablation, as with radio frequency ablation, the points of greatest impedance mismatch are located at the tip of the catheter. Further, the impedance on the catheter side of the device (as distinguished from the power supply or energy source) tends to vary a fair amount as the catheter is moved about during use and as tissue properties change during an ablation procedure. For example, the impedance of the catheter to tissue coupling will vary with the location at which the catheter tip is placed in the heart. It will also vary during the course of a typical ablation procedure due to changes in the tissue properties as the target tissue is ablated and heating of the transmission line components. When the impedance changes, an increased percentage of the power is reflected and the catheter's performance is reduced. By way of example, in a representative application wherein the transmission line is approximately one meter long and is a coaxial transmission line having a diameter of 72 thousandths of an inch (1.8 mm), the power output of a well tuned system may only be in the range of 25-30% of the input power. Of course, the power output is likely to improve as the technology develops, but attenuation is always likely to be a significant concern.

To address the attenuation problem, the applicants proposed a tunable catheter arrangement that facilitates impedance matching in the above referenced parent U.S. patent application Ser. No. 08/062,637. The referenced parent application describes novel mechanisms for tuning the catheter system to facilitate on-line impedance matching between the microwave generator side and the catheter side of the system. In one aspect, the application describes a tuning device located remotely in the power supply. Though this location is convenient from a control standpoint and has been used with success, it is inherently somewhat inefficient. Accordingly, the present invention seeks to expand upon the tuning concepts disclosed in the parent application. More specifically, the present application proposes a variety of tuning solutions that compensate for impedance variations in the vicinity of where the variations are generated.

SUMMARY OF THE INVENTION

Accordingly, it is an object of the present invention to optimize the efficiency of the delivery of energy from the power supply to the targeted tissues.

To achieve the foregoing and other objects and in accordance with the purpose of the present invention, an ablation catheter is disclosed that includes a mechanism for effectively altering the impedance seen by the antenna or the waveguide during use in a controlled manner to tune the catheter. The impedance tuning may be accomplished in a variety of manners including altering the electromechanical configuration of the antenna; moving a material relative to the antenna or vice versa in order to vary the effective impedance during use; and providing a tuning mechanism on the waveguide. In a preferred embodiment, the ablation catheter transmits energy in the microwave frequencies and uses a coaxial transmission line as its waveguide. In certain preferred embodiments, the antenna is helical in nature and is carried by the distal end of the transmission line.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE INVENTION

In a typical microwave ablation catheter system, the system is designed to provide a set impedance. Although the actual set impedance may vary, a typical design impedance on the catheter side of the catheter system may be on the order of 50 ohms. However, as discussed above, the impedance tends to vary a fair amount as the catheter is moved about during use and as tissue properties change during ablation. The impedance variations have a number of sources, however a few of the items which have the greatest effect on impedance variations include the catheter tip location, patient to patient tissue variations, and temperature dependent dielectric properties of catheter components and patient tissues. When the impedance changes, the catheter's performance tends to be well below the optimal performance. The decline in performance is most easily seen in the increase in the reflected power. Due to the inherent inefficiencies of electrically small antennas and the potential of unavoidable reflections from the junction between the coaxial transmission line and the antenna assembly, it is desirable to tune the system with a tuning mechanism in close proximity to the source of the reflected power, ideally at an appropriate location that is a distance of less than one wavelength from the antenna junction. The present application describes several presently preferred embodiments that are capable of providing catheter tip based tuning.

A wide variety of factors will affect the impedance of the antenna. In addition to the external factors previously discussed, the antenna's geometry will have a strong influence on the overall impedance. Some of the factors include the coil diameter, the pitch, the length of wire used, the gap, the wire diameter and cross sectional shape, and the dielectric properties of surrounding mediums. The spacing of the turns of the coil is determined by their pitch or the lead angle ($\alpha$). Of course, the spacing between turns does not need to be constant over the length of the coil. The spacing between the first turn of the antenna coil and the distal face of a shield termination is referred to as the gap. Other catheter factors that influence the antenna's impedance include the composition, mass, location and electrical properties of the other components within the catheter tip. Optimization of the energy coupling between the transmission line and the targeted tissues requires careful selection of the parameters discussed above, each of which can be considered as a variable that may be used to adjust the impedance and energy transmission characteristics of the antenna.

Figure 1:
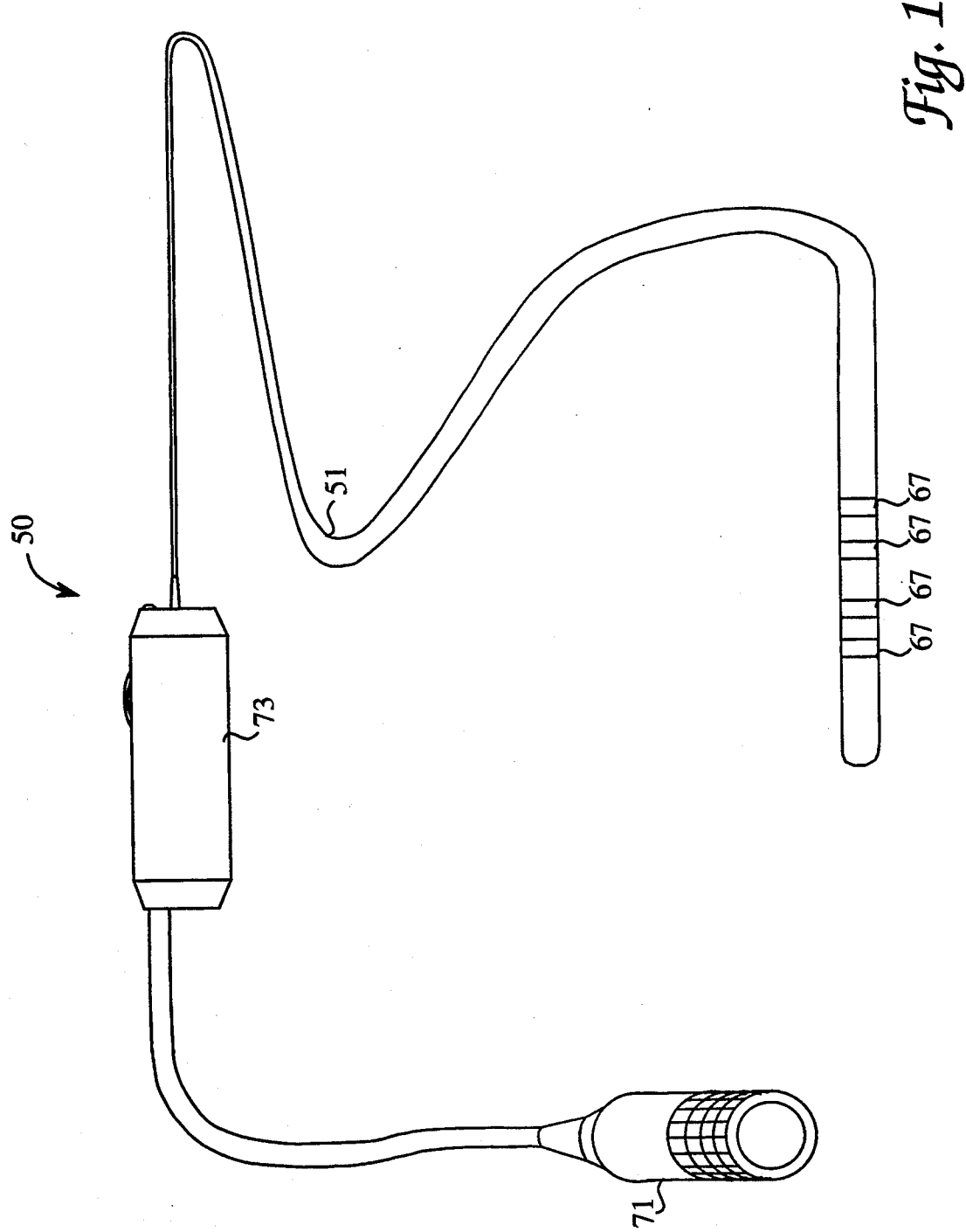
FIG. 1 is a diagrammatic view of an ablation catheter formed in accordance with the present invention.
Figure 8:
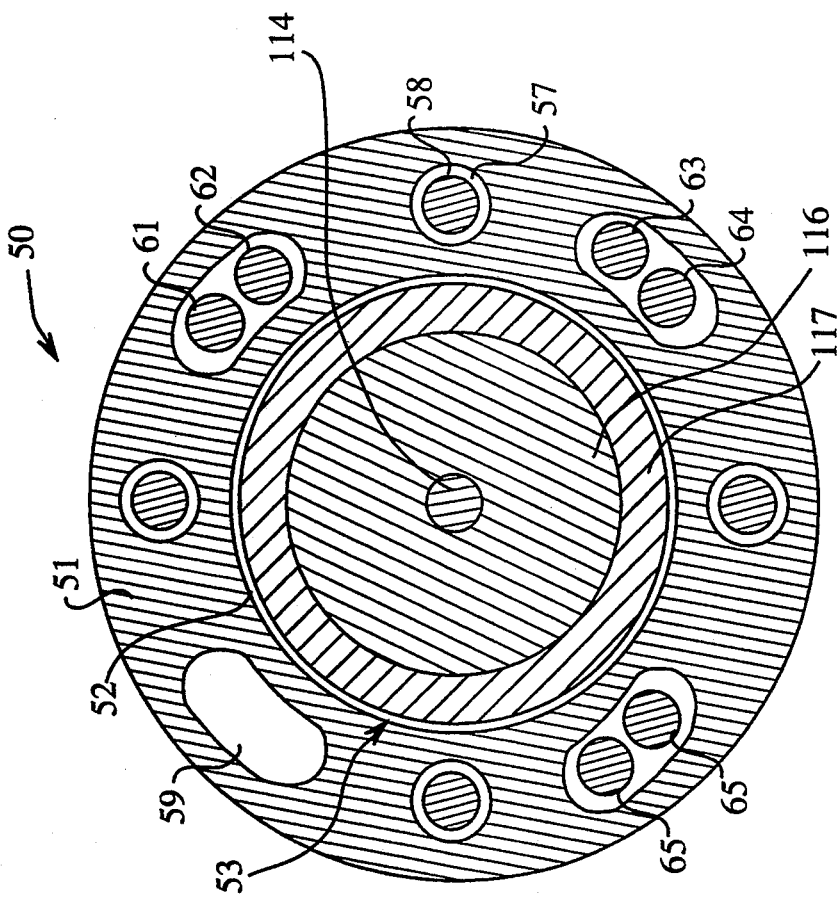
FIG. 8 is a diagrammatic cross sectional view of a tubular member in accordance with the present invention along an uninterrupted portion of the catheter.

Referring initially to FIGS. 1 and 8, a suitable catheter that includes a tunable antenna will be described. The catheter 50 includes outer tubing 51, a coaxial microwave transmission line 53, a helical antenna 56, a stiffener wires 58, a plurality of electrode wires 61–64, thermometry elements 65, steering elements and electrodes 67 and a connector 71. The outer tubing 51 may be made of any suitable material such as medical grade polyolefins, fluoropolymers, or polyvinylidene fluoride. Further, PEBAX resins from Autochem of Germany have been used with success for the outer tubing of the body of the catheter. However, Teflon type products are preferred for the tip. The connector 71 couples the transmission line 53 to an external power supply.

The current thinking is that in order to transmit microwave energy in small diameter environments, the wave guide should be a coaxial cable. Therefore, a coaxial wave guide is selected that is suitable for transmitting microwave energy. A suitable wave guide is the AS450-3050 coaxial cable supplied by Cooner of Chatsworth (Calif.). Of course, the diameter of the coaxial transmission line 53 will vary depending upon the needs of a particular system. However, generally, the larger the diameter, the better the microwave transmission characteristics will be. By way of example, as indicated above, in coronary applications, the catheter diameter is typically limited to approximately 7½ French (approximately 2.5 mm in diameter). In such a system, a wave guide that is approximately one meter long and has a diameter of 72 thousandths of an inch (1.8 mm) works well. The stiffener wires 58 may also represent a mechanical flexure device allowing for flexure control and improved steering. The thermometry elements 65 may take the form of thermocouple wires, fiber optic sensor cables or any other suitable thermometry devices.

An antenna 56 is provided at the distal end of the transmission line. Although the geometry of the antenna may vary in accordance with the needs of a particular application, a helical coil type antenna having a total length (i.e. length of the wire along the coil as opposed to the longitudinal length of the coil) equal to either one eighth or one quarter of the wavelength of the transmitted microwave energy (or a multiple thereof) has been found to work particularly well when the goal is to develop a strong field to the side of the antenna, which is desirable for certain applications. This antenna configuration also exhibits particularly good coupling to the transmission line. In view of this characteristic, the optimal actual length of such an antenna will vary in accordance with the selected frequency. The characteristics of the helical coil type antenna are the result of a variety of characteristics including shield (ground plane) to antenna gap, coil pitch, wire size, wire geometry and coil diameter. It should be appreciated that the actual antenna geometry can be varied widely in accordance with the type of ablation that is desired for a particular application. For example, the helical antenna shown is particularly good at developing a strong electromagnetic field to the side of the catheter tip. On the other hand, a straight antenna tip that extends slightly beyond a shield may be more effective at developing fields that extend from the distal end of the catheter.

A series of electrodes 67 may be provided near the tip of the catheter to monitor the patient's condition and/or the nature of the ablation process. In the described embodiment, the information obtained from the electrodes 67 is transmitted through the power supply to external electronics. Filtering of the signal may be provided as necessary. In alternative embodiments, some of the external electronics could be incorporated into the power supply and/or the power supply could use information obtained from the electrodes in its control scheme.

Figure 2:
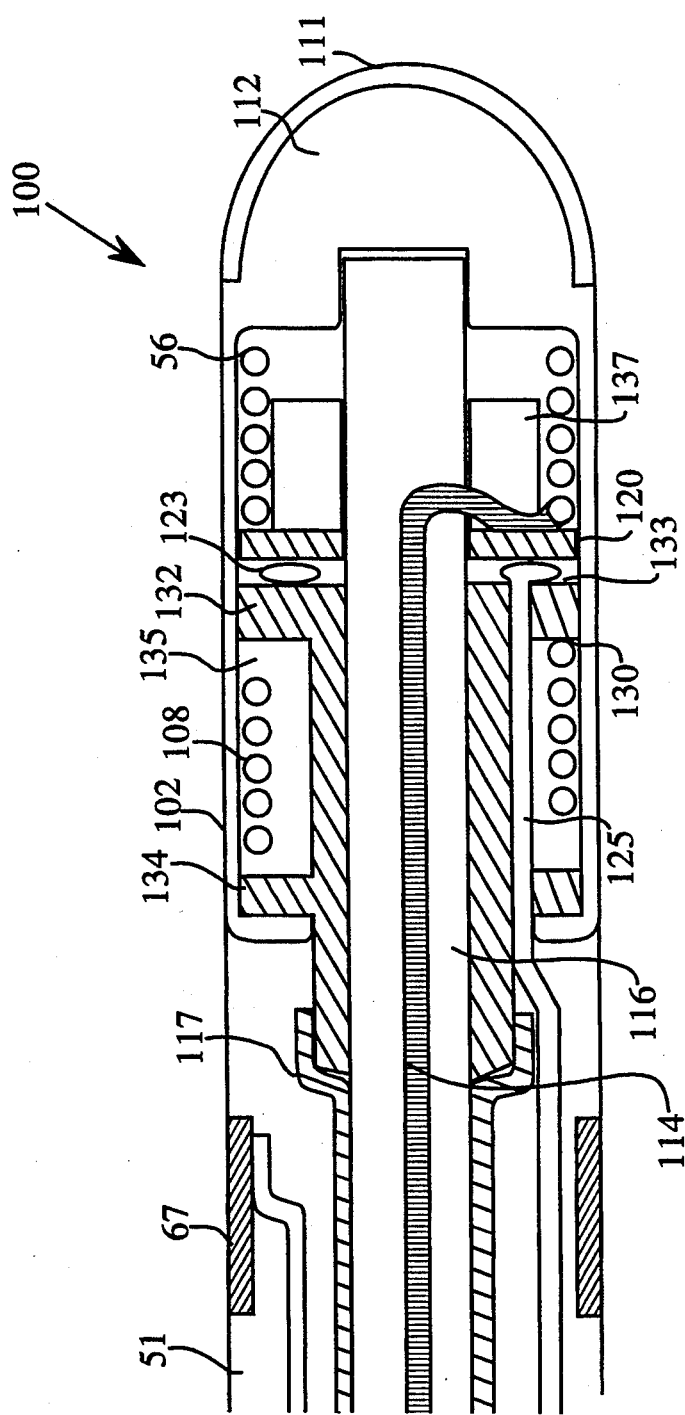
FIG. 2 is a diagrammatic cross sectional side view of the tip portion of one embodiment of an ablation catheter in accordance with the present invention.

Referring next to FIG. 2, a presently preferred embodiment of the invention that includes a tunable antenna will be described. The catheter tip 100 is encased within a insulating shell 102 formed from a dielectric material such as silicone or Teflon. The shell 102 insulates the antenna 56 to avoid the charring and tissue destruction effects that are commonly experienced with exposed (uninsulated) catheter tips. The shell 102 encloses a pair of helical coils which include an antenna coil 56 and a ground coil 108. An electrode 111 is provided at the distal end of the shell and is supported by an enlarged dielectric plug 112 that is formed integrally with the shell 102. The antenna coil 56 is coupled directly to the center conductor 114 of the coaxial transmission line 53 to make a smooth transition between the transmission line and the helical antenna coil 56. In the embodiment shown, the connection is made at the proximal end of the antenna. However, it should be appreciated that the connection may be made at any point along the length of the coil. It should be appreciated that movement of the connection point is expected to have an impact on the electromagnetic field generated by the antenna and upon the impedance characteristics of the antenna. The antenna coil 56 may be formed from a variety of materials that exhibit good conducting and flexibility properties. By way of example, silver plated stainless steel spring wire is an excellent material for this application.

The dielectric support portion 116 of the coaxial transmission line extends beyond the point where the center conductor is attached to the antenna coil 56 so that it extends coaxially through the entire antenna coil and into a supporting recess in the dielectric plug 112. The dielectric support 116 also serves; as a guide for slider 137. Since the field produced by the antenna is very intense on the coil's interior, it is important that the dielectric support material be capable of withstanding intense electromagnetic fields in the microwave frequency range. By way of example, a suitable dielectric material is Teflon, although other suitable materials or mediums could be used as well.

A shield termination 130 is coupled to the shield portion 117 of the coaxial transmission line 53. The shield termination 130 has an enlarged head 132 at its distal surface. Various electrodes and metallic wires are located proximal of the shield termination head for protection from the strong electromagnetic fields generated during use. Thus, the shield termination serves as an electromagnetic shield for the electronics. The shield termination 130 extends proximally beyond the dielectric shell 102 to make a good connection with the shield 117 which anchors the catheter transmission line. The connection can be made using any suitable connection technique such as soldering, brazing or crimping. The shield termination also includes an enlarged anchor portion 134 that mates with the proximal end of the shell to secure the shell in place. The anchor and head portions of the shield termination 130 cooperate to form a bobbin like structure having an opening 135 that receives the ground coil 108. The distal end of the thermometry element 65 (not shown) are positioned behind the head portion 132 of the shield termination. The electrodes 67 are positioned proximally relative to the shell 102. Similarly, the distal end of stiffening/steering wires 58 are positioned proximally relative to the antenna. The reason for the positioning of the thermocouple, the electrodes and wire elements behind the shield is to prevent their interference with the electromagnetic field and vice versa.

To adjust the antenna's impedance, a slidable thrust plate 120 is provided between the proximal end of the antenna coil 56 and the shield termination head 132. The thrust plate 120 is driven by a balloon actuator 123 that is located between the thrust plate and the face 133 of the shield termination. Thus, the shield termination 130 acts as a surface against which the balloon actuator 123 may push in order to regulate the position of the thrust plate. The balloon actuator 123 is fed by a feed tube 125. A slider 137 is provided distal of the thrust plate and serves to balance the thrust plate 120 so that it moves evenly in an orientation that is substantially perpendicular to the longitudinal axis of the catheter. More specifically, the slider is secured to the thrust plate and is closely journaled around the dielectric support 116 to insure that the thrust plate 120 does not wobble as it translates. Electrical properties of the slide 137 may be selected appropriately based upon the needs of a particular catheter.

In one preferred embodiment, the thrust plate 120 is formed from a conductive material in capacitive proximity with the proximal face 133 of the shield head 132. The balloon actuator 123 is then used to vary the distance between the two surfaces. The resulting capacitance interaction between the shield and the thrust plate follows the well known equation:

$$C = keA/d,$$

where "k" is the dielectric constant, "e" is the permittivity constant, "A" is the area of the opposing surfaces, and "d" is the distance between the surfaces. Thus, by varying the distance between the shield's termination head 132 and the thrust plate 120, the apparent impedance of the catheter side of the ablation system can be readily controlled, which permits good impedance matching. It is noted that with this arrangement, the thrust plate 120 is attached to the slider 137 to assure uniform variation of the distance between the facing surfaces of the thrust plate and the shield 130. Further, the proximal end of the antenna coil 56 is attached to the thrust plate 120 and a small gap may be provided between the distal end of the antenna coil 56 and the dielectric plug 112. Therefore, the antenna coil has room to slide back and forth with the thrust plate 120.

In an alternative embodiment, the thrust plate 120 is formed from a non-conductive material such as Teflon and is used to mechanically adjust the length of the antenna coil 56. It should be appreciated that variations in any of the coil's dimensions, including length, width and pitch will vary the impedance at the catheter tip. Accordingly, the antenna's impedance may be adjusted by varying the length of the antenna coil. In this embodiment, the distal end of the antenna coil preferably abuts against or is coupled to the proximal surface of the dielectric plug 112 so that the plug serves as an anchor point for the coil. At the same time, the proximal end of the antenna coil 56 is secured to the thrust plate 120. Thus, movement of the thrust plate back and forth will cause the compression and extension of the antenna coil.

In yet another embodiment of the invention, the slider 137 may be used as a tuning slug. That is, the impedance seen by the antenna may be adjusted by moving the slider back and forth relative to the antenna coil 56. In this embodiment, the antenna coil 56 is not connected to the thrust plate so that it is independent of movement of the thrust plate. To maintain the independence of movement, the diameter of the thrust plate may be reduced, or a space may be provided between the thrust plate 120 and the antenna coil 56. The slider may be constructed of any suitable dielectric, conductive, or ferrite materials to accomplish the objectives of the invention. Depending upon the tuning behavior desired for a particular application. For example, when a dielectric material is use as the slider, the higher its dielectric constant, the greater the range of adjustment for a given mechanical translation.

The ground coil 108 is used to further improve the performance of the antenna assembly. The ground coil 108 is attached to the shield termination head 132 in close proximity to the shield termination face 133. Best results are achieved when the ground coil 108 is a mirror image of the antenna coil 56. Therefore, again a wire length equal to a quarter wavelength (or failing that, an eighth wavelength) is preferred. The ground coil 108 functions similarly to the common "bazooka" configuration frequently used in electrically small microwave antennas. However, such "bazooka" configurations would be too cumbersome to use in this application. A properly sized and positioned ground coil tends to help focus the electromagnetic field and therefore increases penetration at a given power setting.

In certain antenna configurations, it may be desirable to coil the wire of the antenna with a pitch that is smaller than that which would be possible with a round wire. By way of example, to achieve circular polarization with an electrically short helical coil antenna, the following formula described by Stutzman and Thiele in their text entitled "Antenna Theory and Design", John Wiley & Sons (1981) may be used:

$$C = (Pi)D = (2S(\lambda))^{\frac{1}{2}}$$

For a wavelength of 12.25 cm corresponding to 2.45 GHz in free space and a diametric constraint of 2 mm, the pitch, S, would be about 0.016 mm. If the center conductor of the coaxial transmission line feeding the antenna was 0.025 mm, a pitch of 0.016 would not be possible with a round wire. To account for this and preserve the surface area available for current conduction, a rectangular cross section may be used.

The distal electrode 111 is useful for accurately positioning the catheter during an ablation procedure. The primary challenge to the use of a distal electrode is the electrical accessibility and electrical insulation of the electrode. Any conducting material in the field of the antenna will result in distortion of the electrical field and potential conduction of energy away from the antenna in the direction of the power supply end of the catheter. The distal electrode is electrically isolated from the antenna itself and is accessed with a contact wire. A contact wire guide tube (not shown) is passed through the shield termination face in close radial proximity to the balloon actuator feed tube and occupying the gap between the two ends of the balloon actuator. The tube continues through guide holes in the thrust plate 120 and slider 137, and is terminated in the dielectric plug 112. The guide tube is formed from a suitable dielectric material such as Teflon.

A guide wire may be advanced manually or automatically through the region of the antenna and into contact with a recess in the distal electrode 111. Plated stainless steel spring wire is a preferred material for the guide wire. Alternatively, the guide tube may take the form of a fluidic capillary used to transmit pressure to a switch mechanism providing contact between the antenna itself and the distal electrode whereby the positioning signal is read on the center conductor of the microwave transmission line accessed via a coaxial switch or filter arrangement. This alternative can be configured for rapid cycling of the switch mechanism allowing for automatic and periodic sensing timed with intermittent cycling of the microwave power.

Figure 3:
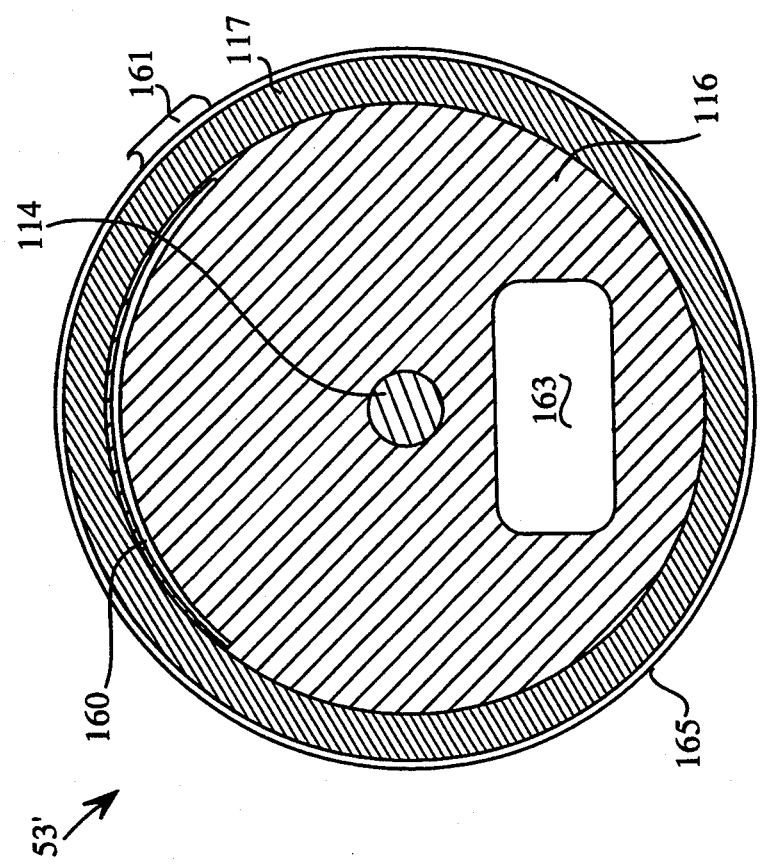
FIG. 3 is a diagrammatic cross sectional view of a coaxial transmission line in accordance with a second embodiment of the present invention which includes a tuning balloon that is suitable for altering the cross section of the coaxial transmission line by deflecting the center conductor.

Referring next to FIG. 3, an alternative embodiment of the invention that includes a quarter wavelength tuner that distorts the coaxial transmission line itself to accomplish tuning will be described. In this embodiment, a tuning balloon 160 is inserted into a quarter wavelength long portion of the coaxial transmission line between the shield 117 and the dielectric support 116. The tuning balloon 160 is placed in close proximity to the location of the impedance mismatch. Preferably adjacent to or within one wavelengh of the antenna junction. The optimal location for the tuner is a function of the impedance characteristics of the antenna itself. Inflation of the tuning balloon 160 presses against the dielectric support 116 creating a side load on the center conductor 114 which in turn distorts the cross section of the transmission line and changes the impedance of the distorted portion. The tuning balloon is longitudinally tapered to facilitate a smooth transition from the undistorted transmission line to the distorted portion. This provides a smooth variation of the characteristic impedance of the line. By way of example, the tuning balloon may be formed from thin wall polyester tubing that is pinched off and sealed at one end. If room permits, it is desirable to have both ends of the tuning balloon tapered. However, in certain applications it may be necessary to have just one or even neither of the ends tapered. The tuning balloon 160 may be filled through port. It should be appreciated that the transmission line 53' shown in FIGS. 3 and 4 will be received within the central lumen of the catheter's outer tubular member 51.

Figure 4:
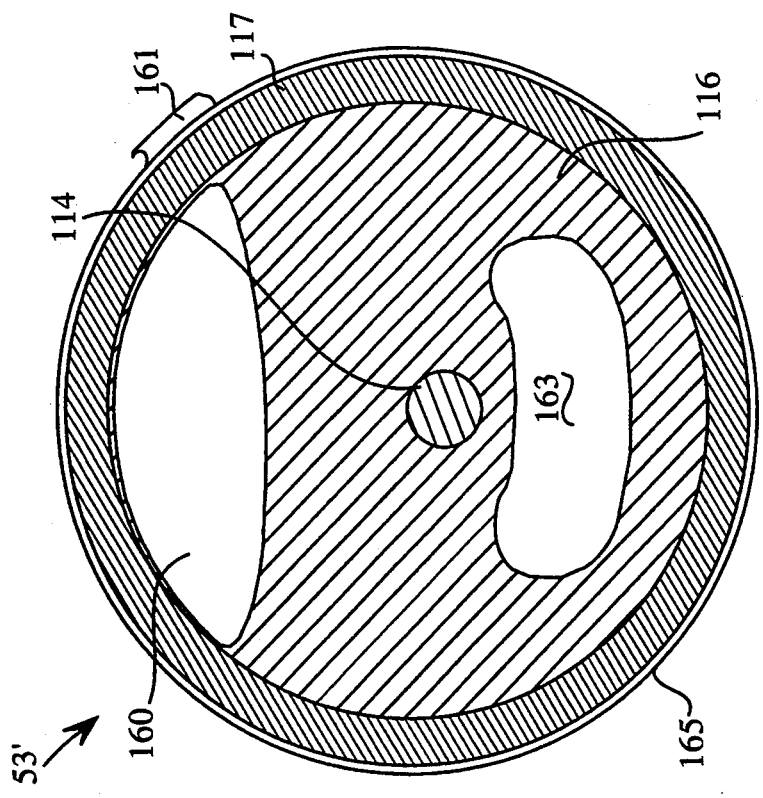
FIG. 4 is a diagrammatic cross sectional view of the transmission line shown in FIG. 3 with the tuning balloon in the inflated position.

A flexure cavity 163 is provided within the dielectric support 116 on the opposite side of the center conductor 114 as the tuning balloon 160. The flexure cavity 163 provides a recess that the center conductor can move towards as the tuning balloon is inflated. Therefore, it serves to minimize distortion of the shield. The lateral motion of the center conductor 114 caused by inflation of the tuning balloon is illustrated in FIG. 4. A shield support 165 serves to protect the integrity of the transmission line shield 117. Thin wall polyester shrink tubing is a suitable material for the shield support. The tuning balloon can be installed from the distal end of the catheter transmission line or from a proximal direction through a hole in the transmission line shield, leakage from which is avoided with an additional grounded sleeve installed in a triaxial fashion. In practice, it is quite difficult to provide a flexure cavity 163, accordingly is preferable to provide an alternative structure that provides the same mechanical effect as the flexure cavity. For example, a foamed or expanded material can be used in the dielectric to absorb the deflection.

The function of the quarter wavelength tuner is to match two structures with differing characteristic impedances. These structures will be matched by a quarter wavelength transmission line when the characteristic impedance of the quarter wavelength transmission line is equal to the geometric means of the impedances of the two mismatched structures. This phenomenon is discussed in Wolff's text "Microwave Engineering and Systems Applications" published in 1988 by John Wiley and Sons. Therefore, for a catheter transmission line with a characteristic impedance of $Z_O$ and an antenna assembly with an equivalent characteristic impedance of $Z_L$. The characteristic impedance, $Z_T$, required for the quarter wavelength tuner is $Z_T = (Z_O Z_L)^{\frac{1}{2}}$. The theoretical value of the transmission line impedance with a shifted center conductor can be calculated using the following formula derived from Transmission Line Design Handbook, by Wadell:

$$Z_O = 0.159 Q^{-\frac{1}{2}} k \cosh^{-1}[R(1.0 - X^2 R^{-2})/2.0r + r/2.0R],$$

where Q is the permittivity constant, k is the dielectric constant, r is the radius of the center conductor, R is the radius of the dielectric material and X is the displacement of the center conductor from the centerline of the transmission line.

Figure 5:
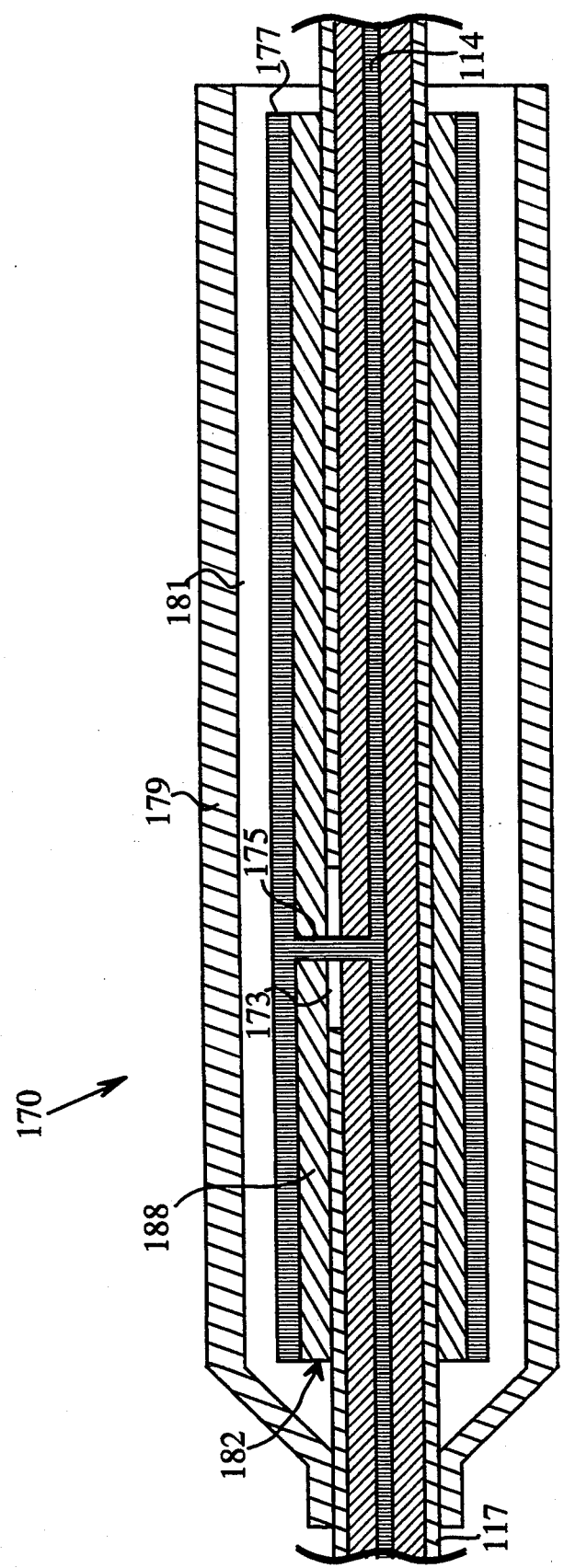
FIG. 5 is a diagrammatic cross sectional side view of a co-axial capacitive tuner connected to the coaxial transmission line in accordance with a third embodiment of the invention.

Referring next to FIG. 5, another alternative embodiment of the transmission line that includes a coaxial capacitive tuner 170 will be described. Although the capacitive tuner 170 may be connected to the transmission line 53 at any location along the length of the transmission line, the performance will be the best when the tuner is located in the vicinity of the impedance variations. That is, close to the antenna assembly. Preferably, the tuner will be positioned within one wavelength of the antenna. The coaxial capacitive tuner includes a slot shaped opening 173 formed in the shield of the transmission line. A post 175 extends through the slot 173 and is connected to the center conductor 114. The post 175 supports a tuning sleeve 177 which is capacitively coupled to the transmission line shield 117. A ground plane shield 179 encloses the tuning sleeve 177 to prevent electromagnetic emissions. An inner dielectric cavity 182 is formed between the transmission line shield 117 and the tuning sleeve 177. An outer dielectric cavity 181 is formed between the tuning sleeve 177 and the ground plane shield 179. In some embodiments, highly insulative dielectric materials 188 are placed in one or both of the dielectric cavities.

The capacitance of the tuner is adjusted to achieve the desired tuning. This adjustment may be accomplished in a wide variety of manners. By way of example, a coaxial balloon located in place of the dielectric material 188 may be used to mechanically vary the distance between the opposing capacitive planes. Alternatively, a coaxial dielectric slug may be moved axially in a capacitor dielectric cavity to effect the desired tuning. The slug may be positioned in either the outer dielectric cavity 181 or the inner dielectric cavity 182. It should be appreciated that a variety of other mechanisms may be provided to vary the capacitance effect between the tuning sleeve 177 and the shields as well. By varying the capacitance, the catheter's effective impedance can be effectively controlled.

In yet another preferred embodiment, a pair of back to back coaxial tuners are provided on the catheter transmission line. This embodiment effectively functions as a double stub tuner and is shown in shown in FIG. 6. In a preferred embodiment, the posts are spaced at three eighths of a wavelength and like the preceding embodiment, the tuner is located at an appropriate distance within a wavelength of the antenna junction. The structure of the coaxial tuners used in this embodiment may be similar to the capacitive tuner discussed above with respect to FIG. 5. However, in the particular embodiments shown in FIG. 6, a tuning slug 193 is positioned between each tuning sleeve 177 and the grounding shield 179. The tuning slug effectively shorts the ground shield 179 to the tuning sleeve 177 to control the catheter's effective impedance. In effect, ground shields 179 form a coaxial cable with tuning sleeve 177 having an impedance matched to the coaxial transmission line 56. In the embodiment shown in FIG. 6, push pull cables 191 are used to position the tuning slug relative to the tuning sleeve. Of course, again, a variety of alternative mechanisms may be provided to accomplish the desired tuning effect.

Figure 6:
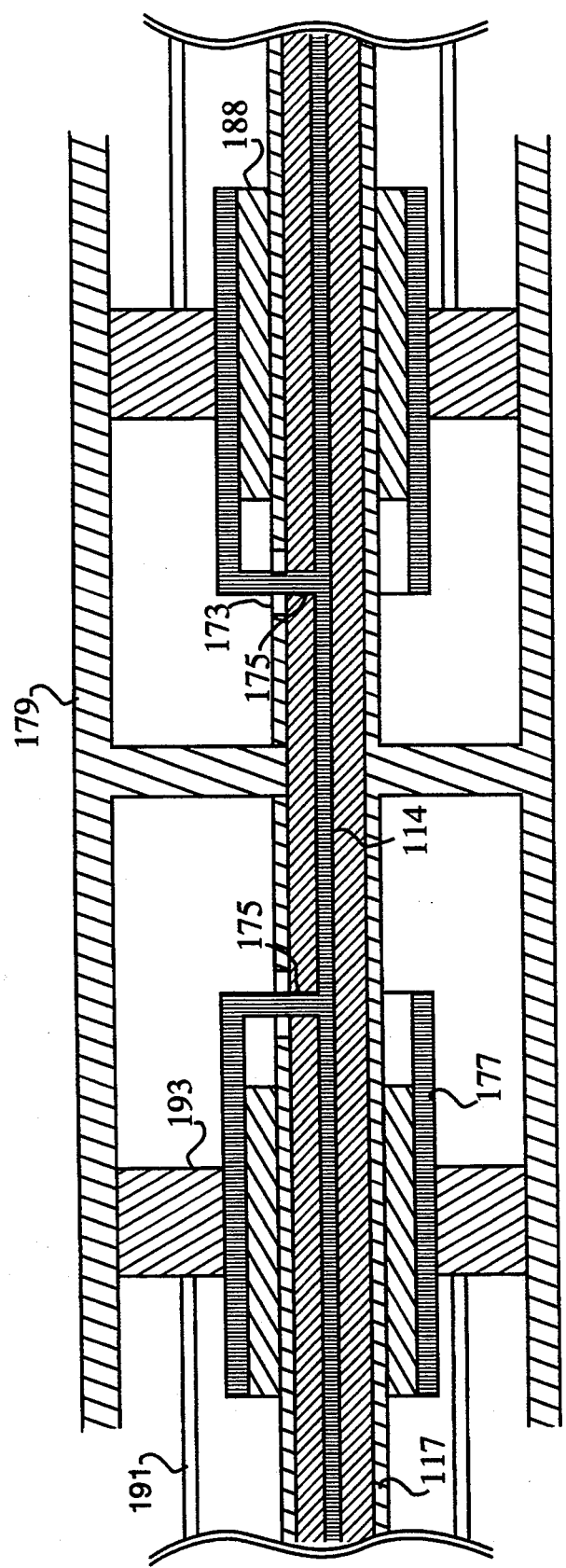
FIG. 6 is a diagrammatic cross sectional side view of a double co-axial capacitive tuner connected to the coaxial transmission line in accordance with a fourth embodiment of the invention.

It should be appreciated that the proportional size of the tuning mechanism shown in FIGS. 5 and 6 have been greatly exaggerated in the diametric dimension in order to clearly show the various parts. In actuality, the entire capacitive tuner must be sized to fit within the central lumen in the outer tubing 51. Thus, the tuning sleeve will typically be relatively closely journaled around the shield with a good dielectric material 188 being placed therebetween. In some cases, the dielectric material may take the form of a dielectric film formed on the tuning sleeve or the shield.

Figure 7:
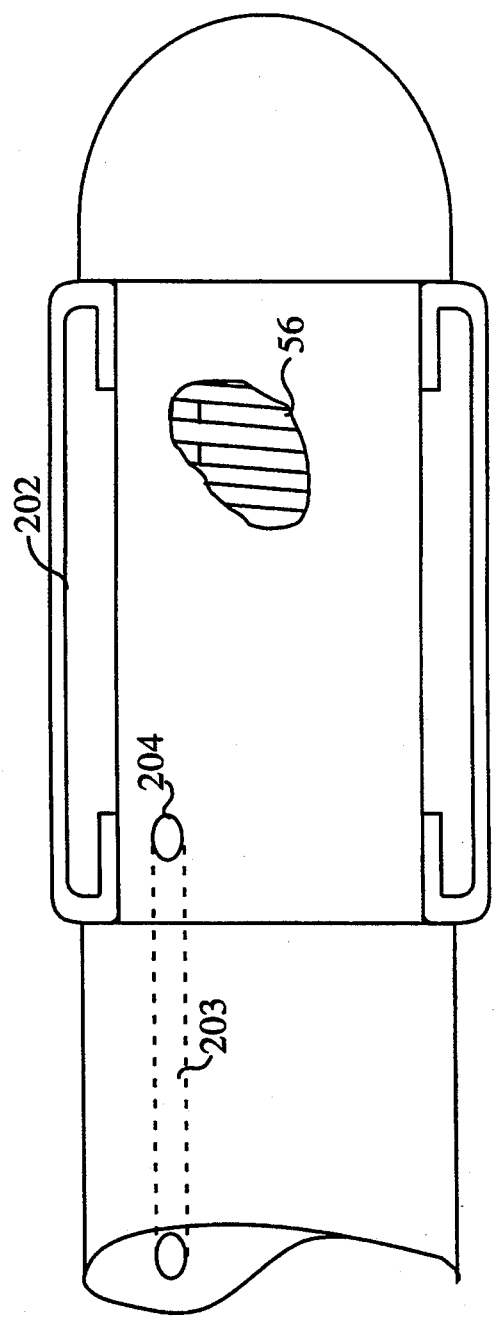
FIG. 7 is a diagrammatic partially cut away side view of the tip portion of an ablation catheter in accordance with a fifth embodiment of the present invention that uses an inflatable balloon.

Referring next to FIG. 7, another embodiment of the invention will be described. In this embodiment, a conventional balloon 202 is journaled about the catheter tip 20 in the region of the antenna coil 56. A fill port 204 in the shell 102 forms a connection between the interior of the balloon 202 and the distal end of a balloon feed lumen 203 similar to the feed tube 125 discussed above with reference to FIG. 2. To tune the antenna, a fluid dielectric is used to inflated (or deflate) the balloon 202.

Referring next to FIG. 8, a catheter construction suitable for use with various embodiments of the present invention will be described in somewhat more detail. As seen therein, the tubular member 51 has an enlarged central lumen 52, a plurality of stiffener lumens 57 and a plurality of elongated component lumens 59. The central lumen 52 is sized to receive the coaxial transmission line 53. The stiffener lumens 57 receive stiffener wires 58. The other various wires (such as the electrode and thermometry wires) may be run through the component lumens 59. Alternatively in embodiments that utilize one or more inflatable balloons, either the stiffener lumens 57 or the component lumens 59 may be used to pass a fluid suitable for inflating the balloon(s).

Figure 9:
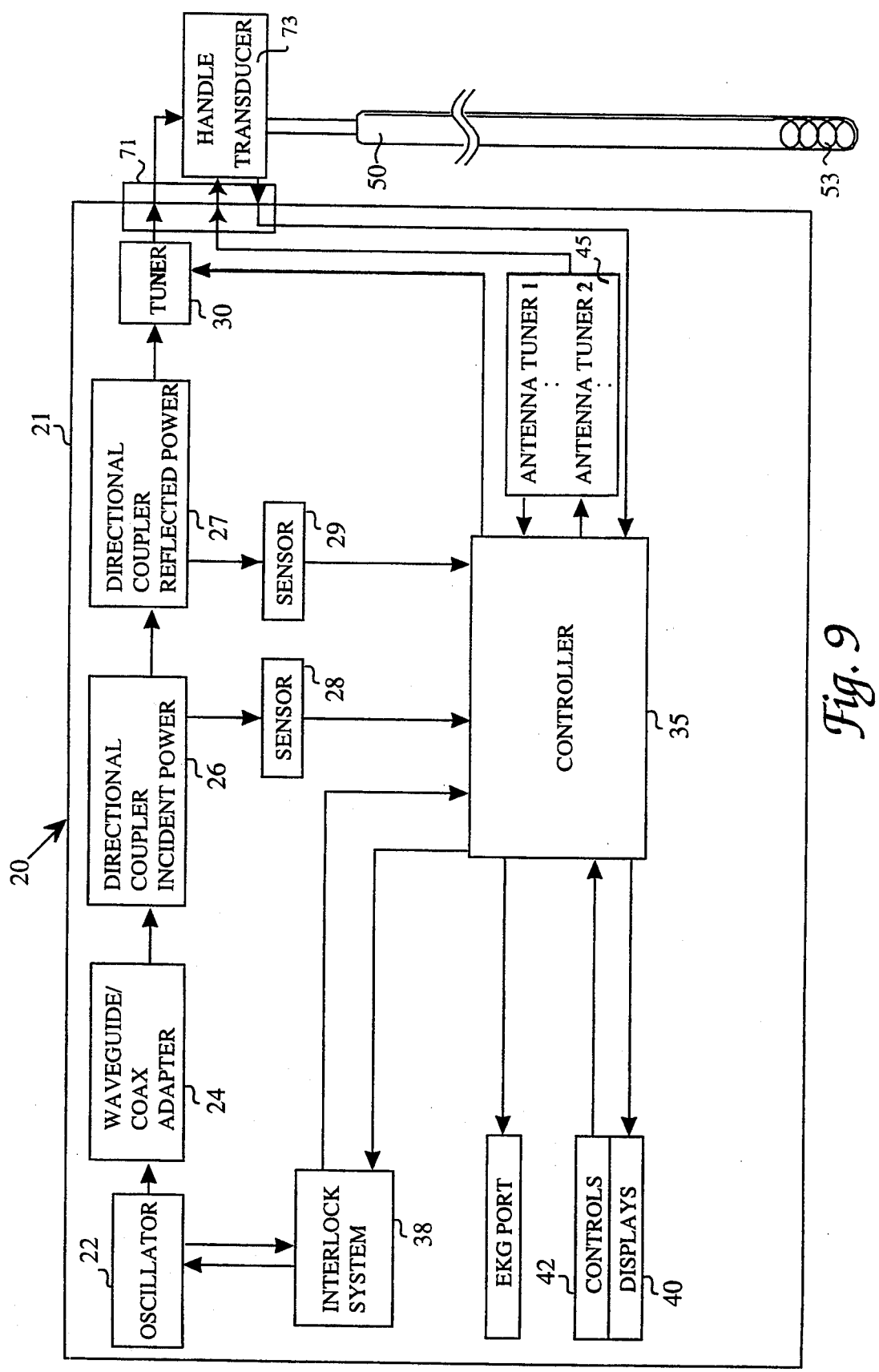
FIG. 9 is a block diagram of a power supply suitable for powering the catheters of the present invention.

Referring next to FIG. 9, a power supply suitable for driving the described ablation catheters well be briefly described. The power supply 20 is designed to generate controlled microwave energy to the catheter 50 which is designed for insertion into the body of a patient. A connector 71 is provided to couple the power supply 20 to the catheter 50. The power supply 20 includes a casing 21 having a microwave generator 22, a waveguide adapter 24, a pair of directional couples 26 & 27 that interface with power monitors 28 and 29 respectively, a tuner 30, a controller 35 and an interlock system 38 all enclosed therein. The front panel 39 of the casing has various displays 40 and controls 42, as well as a port 43 to which conventional EKG equipment can be coupled. Many of the details of such a representative power supply are described in application Ser. No. 08/062,637 which is assigned to the assignee of the present application and is incorporated herein by reference. The primary difference is that the embodiment described in the present application also has a tuning mechanism in the catheter itself that is controlled by antenna tuner 45. The tuner is directed by controller 35.

The microwave generator 22 may take any conventional form. When using microwave energy for tissue ablation, the optimal frequencies are generally in the neighborhood of the optimal frequency for heating water. By way of example, frequencies in the range of approximately 800 MHz to 3 GHz work well. At the time of this writing, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz was chosen. Although any power source may be used, conventional magnetrons of the sort used in microwave ovens are suitable and have been used by the inventor. The microwave energy is transmitted from the microwave generated through a waveguide to coax adapter to a pair of directional couplers 26, 27 used to monitor forward and reflected power respectively. The output of each directional coupler is connected to an associated power sensor 28, 29 which output signals indicative of the forward and reflected power to the controller. Following the directional couplers, the transmission line may be equipped with a stub tuner mechanism 30 that is controlled by the controller as discussed in the above reference application. Downstream from the tuner 30, the power is directed through a quick disconnect jack and plug (connector 71) to the catheter 50 itself. The catheter is equipped with an active tuning mechanism, as discussed above. These mechanisms are controlled either manually or automatically by the antenna tuner 45. System controls are provided for operation of the power supply as is a display for such information as system set points, forward and reflected power, temperatures, etc. The controller 35 may take the form of dedicated logic, but in a preferred embodiment a conventional microprocessor or computer is used.

Figure 10:
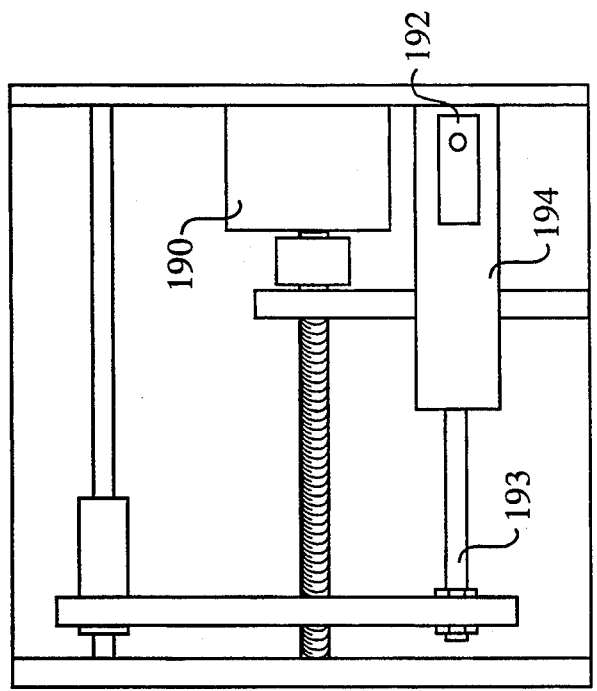
FIG. 10 is a diagrammatic view of a hydraulic control assembly suitable for controlling the pressure within a balloon.

A hydraulic or pneumatic control linkage between the antenna tuner(s) 45 and the catheter is provided with a quick disconnect interface. The convenience of such a quick disconnect should be apparent. The linkage can be transduced in the catheter handle 73 into other energy transmitting alternatives such as torsional wire actuation, axial wire actuation, or electrical actuation as required for any particular application. FIG. 10 illustrates a suitable hydraulic or pneumatic control system. As seen therein, a motor 190 is used to move a plunger 193 within a cylinder reservoir 194 providing either positive or negative pressures for dual directional actuation. The movements of the motor 190 are directed by the controller 35. A pressure sensor 192 provides reactionary feedback to the controller and affords insight into potentially dangerous over pressure conditions. The fluid pressure is transmitted from the cylinder port, through the quick disconnect connector 71, and on to the handle 73 of the catheter where it is transduced as required or transmitted directly to the actuating mechanism. An alternative embodiment uses a pressure reservoir coupled to the catheter via a vented pressure regulator controlled by the controller in a similar manner.

In all of the above embodiments, the controller operates in accordance with a control algorithm structured to minimize reflected power with respect to forward power and set point power. The control algorithm also provides feedback indicative of the system's operation and allows for identification of potentially dangerous fault and alarm conditions.

Although only one embodiment of the present invention has been described, it should be understood that the present invention may be embodied in many other specific forms without departing from the spirit or scope of the invention. Particularly, the invention has been described in terms of an ablation catheter for cardiac applications, however, it should be appreciated that the described small diameter microwave ablation catheter could be used for a wide variety of alternative applications as well. Further, although a variety of antenna based tuning arrangements have been described in detail, it should be appreciated that many others that fall within the spirit and scope of this invention could be used as well. For example, the contact point of the center conductor with the helical antenna coil may be moved axially with respect to the helical coil by use of a sliding contact brush. Alternatively, the mechanical, electrical, capacitive, inductive, and/or resistive properties of any of the antenna components can also be used to aid in the tuning of the system. Further, in some circumstances, it may be desirable to provide a catheter with multiple tuning mechanisms to provide additionally flexibility.

Accordingly, the catheter design, the power supply design and the tuner design may all be modified within the scope of this invention. Therefore, the present examples are to be considered as illustrative and not restrictive, and the invention is not to be limited to the details given herein, but may be modified within the scope of the appended claims.

We claim:

1. A medical catheter comprising:
   a flexible tubular member adapted to be inserted into a vessel in a body of a patient;
   a coaxial transmission line disposed within the tubular member, the transmission line having proximal and distal ends, wherein the proximal end of the transmission line is suitable for connection to a radio frequency energy source;
   a helical antenna carried by the distal end of the transmission line for generating an electric field sufficiently strong to cause tissue ablation; and
   means for altering the geometry of the antenna during use in a controlled manner to alter the effective impedance of the antenna to permit tuning of the catheter during use by compensating for variations in the effective impedance of the catheter that occur during use, the antenna geometry altering means having a portion that is directly or indirectly in contact with the antenna.

2. A catheter as recited in claim 1 wherein the antenna altering means is arranged to alter the length of the antenna.

3. A catheter as recited in claim 1 wherein the antenna altering means is arranged to alter the pitch of at least a portion of the antenna.

4. A catheter as recited in claim 1 wherein the antenna altering means is arranged to alter a diameter of at least a portion of the antenna.

5. A catheter as recited in claim 1 wherein the antenna altering means includes:
   a thrust plate arranged for longitudinal movement within the catheter, the thrust plate being coupled to a first end of the antenna and wherein a second end of the antenna is anchored; and
   actuator means for moving the thrust plate longitudinally relative to the catheter so that movement of the thrust plate causes the antenna compress or extend longitudinally.

6. A medical catheter comprising:
   a flexible tubular member adapted to be inserted into a vessel in the body of a patient;
   a coaxial transmission line disposed within the tubular member, the transmission line having proximal and distal ends, wherein the proximal end of the transmission line is suitable for connection to a radio frequency energy source;
   an antenna carried by the distal end of the transmission line for generating an electric field sufficiently strong to cause tissue ablation; and
   means connected to the catheter for mechanically altering the effective impedance of the antenna during use in a controlled manner to facilitate tuning the catheter by compensating for variations in the effective impedance of the catheter that occur during use.

7. A catheter as recited in claim 6 wherein the impedance altering means includes:
   a thrust plate arranged for longitudinal movement within the catheter, wherein movement of the thrust plate is adapted to cause a variation in the impedance of the antenna; and
   actuator means for moving the thrust plate longitudinally relative to the catheter.

8. A catheter as recited in claim 7 wherein the thrust plate is coupled to a first end of the antenna so that movement of the thrust plate causes the entire antenna to translate longitudinally.

9. A catheter as recited in claim 7 wherein the thrust plate is coupled to a first end of the antenna and a second a second end of the antenna is anchored so that movement of the thrust plate causes the antenna to compress or extend longitudinally.

10. A catheter as recited in claim 7 wherein the actuator means includes an inflatable balloon.

11. A catheter as recited in claim 7 wherein the coaxial transmission line includes a shield, the catheter further comprising a shield termination located at a distal end of the shield, and wherein the thrust plate is capacitively coupled to the shield termination.

12. A catheter as recited in claim 6 wherein the impedance altering means includes:
   a slug arranged for longitudinal movement within the catheter in the region of the antenna for causing variations in the impedance of the antenna; and
   actuator means for moving the slug longitudinally relative to the catheter.

13. A catheter as recited in claim 12 wherein the coaxial transmission line includes a center conductor, a dielectric support portion and a shield, and wherein the slug is journaled about the dielectric support.

14. A catheter as recited in claim 6 further comprising a shield termination that is spaced apart from the antenna, wherein the impedance altering means is arranged to alter the spacing between the shield termination and the antenna.

15. A catheter as recited in claim 6 wherein the catheter is adapted for the transmission of microwave energy.

16. A medical catheter system comprising:
   a catheter as recited in claim 6;
   a power supply that serves as said energy source, the power supply having an electromagnetic energy generator capable of generating radio frequency energy at said predetermined wavelength; and
   a connector for coupling the electromagnetic energy generator to the transmission line.

17. A catheter system as recited in claim 16 further comprising means for detecting power reflected from the catheter side of the catheter system and the means for altering the impedance of the antenna includes a tuner controller that is arranged to alter the impedance of the catheter during use to minimize reflected power.

18. A medical catheter comprising:
a flexible tubular member adapted to be inserted into a vessel in the body of a patient;
a coaxial transmission line disposed within the tubular member, the transmission line having proximal and distal ends, a center conductor, a dielectric material journaled about the center conductor and a shield, wherein the proximal end of the transmission line is suitable for connection to a microwave energy source;
an antenna carried by the distal end of the transmission line for generating an electric field sufficiently strong to cause tissue ablation; and
means connected to the catheter for mechanically altering the impedance of the transmission line during use in a controlled manner to facilitate tuning the catheter by compensating for variations in the effective impedance of the catheter that occur during use.

19. A catheter as recited in claim 18 wherein said impedance altering means includes an inflatable balloon positioned within the flexible tubular member for distorting the cross section of a portion of the transmission line.

20. A catheter as recited in claim 19 wherein said balloon is tapered on at least one end to provide a smooth transition between an undistorted portion of the transmission line and the distorted portion of the transmission line.

21. A catheter as recited in claim 19 wherein the balloon is positioned in close proximity to the antenna within a distance equivalent to the distance of one wavelength of the microwave energy carried by the transmission line during use.

22. A catheter as recited in claim 18 wherein said impedance altering means includes a coaxial tuner coupled to the transmission line.

23. A catheter as recited in claim 22 wherein said coaxial tuner includes a tuning sleeve journaled about and in coaxial communication with said transmission line shield.

24. A catheter as recited in claim 22 wherein said coaxial tuner further comprises a ground plane shield that encloses the tuning sleeve to prevent electromagnetic emissions from the capacitive tuner, the ground plane shield being electrically coupled to said transmission line shield.

25. A catheter as recited in claim 24 wherein said coaxial tuner includes a tuning slug connected between said ground plane shield and tuning sleeve.

26. A catheter as recited in claim 22 wherein said coaxial tuner is a capacitive tuner.

27. A catheter as recited is claim 26 further comprising a balloon for varying the capacitance between the tuning sleeve and one of said shields.

28. A catheter as recited in claim 26 further comprising a longitudinally moveable slug for varying the capacitance between the tuning sleeve and one of said shields.

29. A catheter as recited in claim 18 wherein said impedance altering means includes a double coaxial tuner coupled to the transmission line.

* * * * *